United States Patent [19]

Coombs

[11] Patent Number: 4,753,892

[45] Date of Patent: Jun. 28, 1988

[54] PROCESS FOR FORMING A CONTINUOUS SOLUTION GRADIENT

[76] Inventor: David H. Coombs, 650 Churchill Row, Fredericton, New Brunswick, Canada, E3B 1P6

[21] Appl. No.: 879,075

[22] Filed: Jun. 26, 1986

[51] Int. Cl.[4] .................... G01N 33/48; G01N 33/483

[52] U.S. Cl. ...................................... 436/183; 436/45; 422/258

[58] Field of Search ........................ 422/256, 258–259, 422/72; 23/306; 436/45, 183; 366/219, 220, 232, 235; 210/787, 789, 927

[56] References Cited

U.S. PATENT DOCUMENTS

| | | | |
|---|---|---|---|
| 3,519,400 | 7/1970 | Anderson | 210/789 |
| 3,936,272 | 2/1976 | Saltarelli | 436/172 |
| 4,015,775 | 4/1977 | Rohde | 210/789 |
| 4,066,407 | 1/1978 | Lupica | 436/45 |
| 4,173,925 | 11/1979 | Leon | 366/232 |
| 4,281,936 | 8/1981 | Schotter et al. | 366/233 |
| 4,360,150 | 11/1982 | Ishimaru et al. | 494/16 |
| 4,479,720 | 10/1984 | Mochida et al. | 436/45 |

FOREIGN PATENT DOCUMENTS

| | | | |
|---|---|---|---|
| 0208666 | 12/1983 | Japan | 436/45 |

*Primary Examiner*—Barry S. Richman
*Assistant Examiner*—Timothy M. McMahon
*Attorney, Agent, or Firm*—Louis E. Marn

[57] ABSTRACT

A process and apparatus for generating a continuous solution gradient wherein solutions of differing concentrations are layered in a tube and the tube disposed at an angle with respect to the vertical and is rotated for a predetermined period of time thereby to generate a continuous solution gradient, i.e. continuous variation in concentration between the concentration of the initial solutions.

14 Claims, 1 Drawing Sheet

PROCESS FOR FORMING A CONTINUOUS SOLUTION GRADIENT

BACKGROUND OF THE INVENTION (1) Field of the Invention

This invention relates to a process and apparatus for forming solution gradients, and more particularly to a novel process and apparatus for generating a continuous solution gradient.

(2) Description of the Prior Art

Separation of macromolucules (proteins, DNA and RNA) and larger aggregates, such as viruses and cells, has been and continues to be one of the primary objectives in biochemical research. Perhaps the oldest and still most widely used separation techniques is solution gradient density centrifugation comprising three basic steps: forming a solution gradient, e.g. of sucrose in a tube; centrifuging a sample into the gradient; and recovering the now separated samples from various positions in the gradient-containing tube, sometimes referred to as fractionation.

The term "gradient" implies a continuous variation in concentration from top to bottom, e.g. 5 to 45% sucrose. The gradient performs two critical functions. First and foremost, the gradient prevents mixing in a vertical direction. During acceleration and deceleration of the tube in the centrifuge, a mild degree of mixing is induced which, if unchecked by the gradient, would thoroughly mix the contents in the tube. The gradient, however, prevents such mixing of the density differential between adjacent layers. Secondly, heavier sucrose solutions are much more viscous than light sucrose solutions and consequently, there is established a viscosity gradient. Such a viscosity gradient is useful because "g" forces are greatest at the bottom of the tube (highest radius from the center of rotation) and the increased viscosity effectively cancels the increased "g" forces giving a nearly uniform rate of molecule or particle migration from top to bottom, and consequently one can predict the position of desired molecule at the end of a run.

One of the most serious problems in the constructions of sucrose gradients is reproducibility. It is apparent that the rate of migration of any molecular species through a gradient is subject to the cumulative effects of bouyancy and viscosity of the gradient. Since these two parameters are caused by the shape of the sucrose gradient itself, tube to tube variation in the gradient will produce tube to tube variation in the final position of any molecular species. Often, it is desired to determine whether subtle changes have occurred in the size or shape of cell components, and with very reproducible gradients, such differences may be detected. By the same token, the absolute shape of the gradient is less important so long as the gradient is reprodicible.

There has been a steady but slow evolution in the techniques used to form sucrose gradients beginning with the laborious manual layering of one solution after another into a tube requiring a plurality of pipettes, a steady hand and mountains of patience and time. Such technique was quickly supplanted with a technique similar to chromatographic technology wherein two solutions, in this case the highest and lowest sucrose concentration in a desired gradient, are measured into two adjacent chambers. The mixing chamber (heavy sucrose) is connected to a centrifuge tube on one side and the other chamber (light sucrose) on the other side. As the mixing chamber's contents empty into the centrifuge tube, the contents of the other chamber enter and gradually lower their sucrose concentration. As the chambers empty, the ouflow approaches the light chamber's concentration. Such chromatography-like technology is the most commonly used technique and produces either linear or exponential gradients with minor modifications, but has two major drawbacks, i.e. time and reproducibility. When more than one gradient is desired, the outflow must be partitioned, and nothing has yet been developed that will insure exactly the same flow into each tube. Consequently, a user must watch the level in each tube, clamping off the fast ones until the slow ones catch up, etc. Additionally, there will be slight differences between the gradient in the various tubes because of constant flow adjustments.

Another technique currently in use is a freeze-thaw method wherein a homogenous solution is introduced into a centrifuge tube and the tube is subjected to a plurality of freeze-thaw cycles. Such freeze-thaw method suffers from a serious drawback in that while the freezing and thawing produces a gradient (ice floats and excludes solute molecules from the pure water matrix), any buffer is subjected to the same forces and also ends up as a gradient, producing numerous potential artificacts. Reproducibility is poor because no two tubes thaw out exactly the same way, and also because the gradients decay with time.

OBJECTS OF THE INVENTION

It is an apparatus of the present invention is to provide a novel process and apparatus for generating continuous solution gradients.

Another object of the present invention is to provide a novel process and apparatus for generating continuous solution gradients of faithful reproducibility.

Still another object of the present invention is to provide a novel process and apparatus for generating continuous solution gradients in short periods of time.

Yet another object of the present invention is to provide a novel process and apparatus for generating continuous solution gradients obviating the necessity of personal supervision.

A further object of the present invention is to provide a novel process and apparatus for simultaneously generating a plurality of continuous solution gradients.

A still further object of the present invention is to provide a novel process and apparatus for generating continuous solution gradients using reliable equipment components.

Yet another object of the present invention is to provide a novel process and apparatus for generating continuous solution gradients of extended useful life prior to gradient decay.

SUMMARY OF THE INVENTION

These and other objects of the present invention are achieved by a novel process and apparatus for generating a continuous solution gradient wherein solutions of differing concentrations are layered in a tube and the tube disposed at an angle with respect to the vertical and is rotated for a predetermined period of time thereby to generate a continuous solution gradient, i.e. continuous variation in concentration between the concentration of the initial solutions.

BRIEF DESCRIPTION OF THE DRAWINGS

A better understanding of the present invention as well as other objects and advantages thereof will become apparent upon consideration of the detailed disclosure thereof, especially when taken with the accompanying drawings wherein.

DETAILED DESCRIPTION OF THE INVENTION

Figure 1:
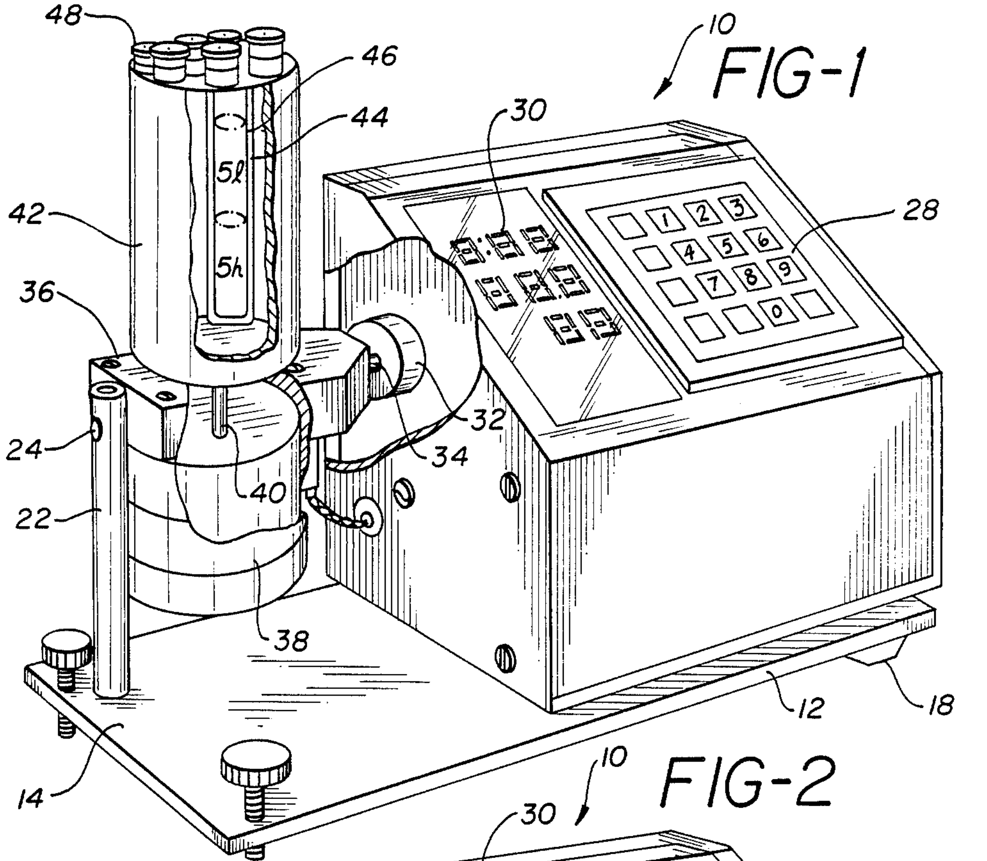
FIG. 1 is an isometric view, partially cut away, of a continuous gradient generating assembly of the present invention.
Figure 2:
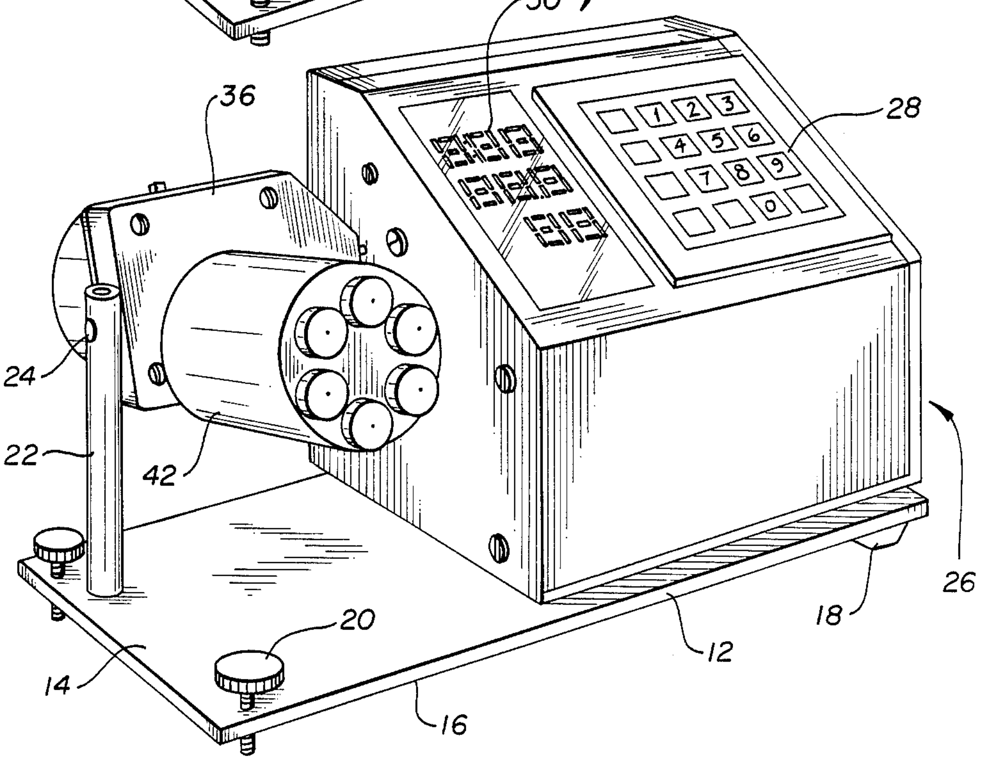
FIG. 2 is an isometric view of the continuous gradient generating assembly in a rotating mode.

Referring now to the drawings, there is illustrated a continuous gradient generating assembly, generally indicated as 10, for effecting the process of the present invention and comprised of a rectangularly-shaped base member 12 having an upper surface 14 and a lower surface 16. On the lower surface 16 of the rectangularly-shaped base member 12, there are positioned leg members 18 (one shown) disposed proximate one side thereof. On the other side of the rectangularly-shaped base member 12, there are provided thumb-type screw members 20 disposed in threaded orifices (not shown) formed in the rectangularly-shaped base member 12 for leveling of the continuous gradient generating assembly 10.

Extending upwardly from the rectangularly-shaped base member 12 on a side thereof proximate the thumb-type screw members 20, there is positioned a vertically-diposed cylindrically-shaped support member 22 having a channel 24 formed in an upper end portion therein perpendicularly-disposed to the axis of the vertically-disposed cylindrically-shaped support member 22. On the other side of the rectangularly-shaped base member 12, there is positioned an operating console member, generally indicated as 26, having a keyboard 28, digital read-out members 30 and concomitant electronics (not shown) including a central processing unit (CPU) and related microprocessors. Within the operating console member 26 there is mounted an electric motor 32 having a shaft 34 and mounted to a side wall of the operating console member 26. The shaft 34 extends horizontally towards and is disposed in the channel 24 of the vertically-disposed cylindrically-shaped support member 22 and is mounted for rotation within the channel 24 of the vertically-disposed cylindrically-shaped support member 22.

To the shaft 34 intermediate the vertically-disposed cylindrically-shaped support member 22 and the side wall of the operating console member 26, there is mounted a support plate member 36 for rotation with the shaft 34 about the horizontal in response to rotation of the commutator of the electric motor 32 as more fully hereinafter discussed. To a bottom surface of the support plate member 36 there is mounted an electric motor 38 including a shaft 40 mounted to a commutator thereof and journaled for rotation in a bearing member (not shown) disposed in the support plate member 36. To the shaft 40 extending above the support plate member 36, there is mounted a tube holder 42 having a plurality of cylindrically-shaped channels 44 disposed radially about a center axis of the tube holder 42. In the position illustrated in FIG. 1, the support plate member 36 is disposed in the horizontal plane with the shaft 40 of the electric motor 38 and the tube holder 42 mounted to the shaft 40 being perpendicularly disposed thereto, i.e. in the vertical. Rotation of the shaft 34 of the electric motor 32 causes the support plate member 36 to rotate about the horizontal thereby causing the tube holder 42 to rotate in a vertical plane perpendicular to the horizontal, as more fully hereinafter discussed. Rotation of the shaft 40 of the electric motor 38 causes the tube holde 42 to rotate in an axis of the vertical plane determined by the preselect rotation of the shaft 34 of the electric motor 32.

To facilitate an understanding of the process of the present invention, the process of the present invention will be described with reference to the formation of a continuous sucrose gradient. It will be understood by one skilled in the art that the process of the invention may use any tube size as well as the fact that continuous solution gradients may be formed of solutions other than sucrose, e.g. Ficoll, Percoll, Ficoll-PAQUE (registered trademarks of Pharmacia Laboratories).

Equal volumes of solutions representing a solution of low concentration ($S_l$) and a solution of high concentration ($S_h$) are layered in a tube 46 generally with the tube 46 in a vertical position. It has been observed that premixing of the solutions may be minimized by first introducing the solution of the lower concentration ($S_l$) into the tube and then introducing into the lower end portion of the tube 46 by cannula syringe the solution of the higher concentration ($S_h$) thereby floating the solution of the lower concentration onto the solution of the higher concentration. To initially establish optimum processing conditions for a particular continuous solution gradient, a dye is admixed in the solution of higher concentration to permit visual observation of gradient formation for any such gradient system, as more fully hereinafter discussed.

After layering of the solutions, the tube 46 is enclosed, preferably using a stopper 48 having a channel (not shown) configured to permit the removal of air from the tube during insertion of the stopper 48 into the open end of the tube 46 in a manner which eliminates any gaseous phase in the tube 46 at completion of the act of insertion of the stopper 48 into the tube 46. Any gaseous phase in the tube 46 is deleterious to gradient formation. The tube 46 is thereupon inserted into one of the cylindrically-shaped channels 44 of the tube holder 42 and the tube holder 42 is then inclined from the vertical in response to rotation of the shaft 34 by the electric motor 32 to an angle to the vertical generally of from about 50° to 89.9°. It has been found that a particular preferred angle is defined by the tube with respect to the vertical when the meniscus formed between the layers first contacts the lower end portion of that end of the stopper 48 inserted into the tube 46, i.e. the meniscus extends laterally across the tube 46 in contact with the lower end portion of the stopper 48.

Upon reaching a predetermined angle of inclination, the tube holder 42 is caused to be rotated in response to rotation of the shaft 40 of the electric motor 38 by energizing the field thereof. The tube 46 is caused to be rotated for a predetermined period of time, generally of from about 1.5 to 5 minutes at a rotational speed of from about 10 to about 25 RPM's during which time the solution of the higher concentration is caused to rise along the inner tube wall and by such contact with the solution of lower concentration flowing over the interface therebetween there is formed a continuous solution gradient. Once the continuous gradient is established, the tube holder 42 is righted to the vertical and the tube 46 removed from the channel 44 for use in a subsequent protocol.

An important aspect of the present invention, in addition to establishing a preferred predetermined tilt angle, is a requirement to establish a predetermined time of rotation for any given rotational speed. For this aspect, visual reliance is placed upon the dye and its migration from the higher concentrated solution into the lower concentrated solution. The formation of a continuous solution gradient is widened by the dye extending to the top of the lower concentrated solution. Upon reaching the point at which the dye has completed initial migration into the solution of lower concentration, rotation of the tube should be discontinued. Extended rotation of the tube, e.g. more than about 5 seconds after observation of migration, should be avoided, since degradation of the continuous solution gradient will thereafter begin and solution homogeneity result with uncontrolled time for discontinuing rotation of the tube.

It will be understood that at low rotational speeds the time of formation of the continuous solution gradient is longer than at higher rotational speeds, and that there are lower and upper limits of rotational speed at which a continuous solution gradient may not be efficaciously formed. Generally, at rotational speeds in excess of about 60 RPM, usable gradients may not be formed. While in the apparatus of the present invention the tube 46 in which the continuous solution gradient is being formed is positioned in a chamber displaced from the axis of rotation of the tube holder 42, the tube 46 may be rotated about its axis with like results. Additionally, while the use of a dye has been described in initial determinations of tilt angle time periods for rotation of the tubes, etc. in a visual determination, it will be understood that other methods for determining such process conditions will be understood by one skilled in the art. It will also be understood that the configuration of the tube in which the continuous solution gradient is to be formed is also important in the determination of appropriate processing conditions. Once having established processing conditions for generating a specific continuous solution gradient from specific solutions using a dye, the resulting processing conditions, i.e. tilt angle, rotational speed and duration of rotation, etc., may be readily introduced as required into the central processing unit or may be preprogrammed and accessed by appropriate language to the CPU thereby to insure faithful reproduction of specific solution gradients from specific initial solutions.

While the invention herein has been described in connection with exemplary embodiments thereof, it will be understood that many modifications will be apparent to those of ordinary skill in the art and that this application is intended to cover any adaptations or variations thereof. Therefore, it is manifestly intended that this invention be only limited by the claims the the equivalents thereof.

What is claimed is:

1. A process for generating a continuous solution gradient which comprises the steps of:

(a) introducing into a tube solutions of differing concentrations of a like solute/solvent system in a manner to layer said solutions therein;

(b) inclining said tube to an angle with respect to the vertical;

(c) rotating said tube about an axis at said angle with respect to the vertical for a sufficient time and at a sufficient speed to form a continuous solution gradient; and (d) discontinuing step (c) after formation of said continuous solution gradient.

2. The process for generating a continuous solution gradient as defined in claim 1 wherein said tube is inclined to an angle of from 50° to about 89.9° from said vertical.

3. The process for generating a continuous solution gradient as defined in claim 1 wherein said solutions of differing concentrations are sucrose solutions.

4. The process for generating a continuous solution gradient as defined in claim 1 wherein said tube is rotated at from 10 to 25 revolutions per minute.

5. The process for generating a continuous solution gradient as defined in claim 4 wherein sid rotation is about 15 revolutions per minute.

6. Theprocess for generating a continuous solution gradient as defined in claim 1 wherein said solutions of differing concentrations are of a low density and of a high density and are sequentially introduced into said tube whereby said solution of low density is introduced prior to said solution of high density.

7. The process for generating a continuous solution gradient as defined in claim 6 wherein said solution of high density is introduced by a cannula syringe in a lower portion of said tube beneath said solution of low density.

8. The process for generating a continuous solution gradient as defined in claim 1 wherein a dye is admixed prior to step (a) with one of said solutions of differing concentrations.

9. The process for generating a continuous solution gradient as defined in claim 8 wherein step (c) is effected for a predetermined time established by migration of said dye into the other solution.

10. The process for generating a continuous solution gradient as defined in claim 9 wherein said dye is admixed in a solution of high density of said solutions of differing concentrations.

11. The process for generating a continuous solution gradient as defined in claim 1 wherein said tube is sealed between step (a) and step (b).

12. The process for generating a continuous solution gradient as defined in claim 11 wherein said tube is sealed in a manner such that no gaseous phase is in said tube.

13. The process for generating a continuous solution gradient as defined in claim 11 wherein said tube is sealed by a stopper.

14. The process for generating a continuous solution gradient as defined in claim 13 wherein said tube is inclined to an angle whereat a meniscus formed between said solutions contacts a lower portion of said stopper.

* * * * *